US008006543B2

(12) United States Patent
Pernel

(10) Patent No.: US 8,006,543 B2

(45) Date of Patent: Aug. 30, 2011

(54) DEVICE FOR MEASURING THE PERMEATION OF A HOLLOW BODY SUCH AS A CONTAINER

(75) Inventor: Yann Pernel, Octeville sur mer (FR)

(73) Assignee: Sidel Participations, Octeville-Sur-Mer (FR)

( * ) Notice: Subject to any disclaimer, the term of this patent is extended or adjusted under 35 U.S.C. 154(b) by 391 days.

(21) Appl. No.: 12/158,917

(22) PCT Filed: Dec. 20, 2006

(86) PCT No.: PCT/FR2006/002813

§ 371 (c)(1), (2), (4) Date: Jun. 23, 2008

(87) PCT Pub. No.: WO2007/077335

PCT Pub. Date: Jul. 12, 2007

(65) Prior Publication Data

US 2009/0000355 A1 Jan. 1, 2009

(30) Foreign Application Priority Data

Dec. 22, 2005 (FR) .................................... 05 13165

(51) Int. Cl.
*G01N 15/08* (2006.01)

(52) U.S. Cl. .......................................................... 73/38

(58) Field of Classification Search ...................... 73/38
See application file for complete search history.

(56) References Cited

U.S. PATENT DOCUMENTS 6,857,307 B2 * 2/2005 Gebele et al. .................... 73/38
6,964,191 B1 11/2005 Tata
2002/0162384 A1 * 11/2002 Sharp et al. ...................... 73/38
2002/0194899 A1 12/2002 Gebele et al.
2004/0040372 A1 3/2004 Plester et al.
2004/0177676 A1 9/2004 Moore

FOREIGN PATENT DOCUMENTS

DE 102 40 295 A1 4/2004
DE 103 50 519 A1 6/2005
FR 2 844 596 A1 3/2004
WO 02/088657 A2 11/2002

OTHER PUBLICATIONS

International Search Report for PCT/FR2006/002813 dated Jun. 4, 2007.

* cited by examiner

*Primary Examiner* — Hezron Williams
*Assistant Examiner* — Nathaniel Kolb
(74) *Attorney, Agent, or Firm* — Sughrue Mion, PLLC

(57) ABSTRACT

Device for measuring the permeation of a hollow body provided with an opening such as a neck in particular, this device comprising a chamber in which the follow body is placed, on a support; this hollow body, when placed on its support, together with the chamber defining an internal space and an external space, the device being provided with means for providing sealing between the internal space and the external space, the sealing means comprising three seals, namely a first seal, a second seal termed the intermediate seal, and a third seal, these three seals being housed in grooves belonging to the body of the support, these seals projecting from the side edge of the support and being able and configured to bear against the internal face of the opening of the hollow body; the body of the support, the opening of the object and the seals thus define two spaces positioned between the internal space and the external space, a first space being bordered by a first seal and an intermediate seal, the second space being defined by the intermediate seal and a third seal.

10 Claims, 3 Drawing Sheets

DEVICE FOR MEASURING THE PERMEATION OF A HOLLOW BODY SUCH AS A CONTAINER

CROSS REFERENCE TO RELATED APPLICATION

This application is a National Stage of International Application No. PCT/FR2006/002813 filed on Dec. 20, 2006, claiming priority based on French Patent Application No. 05 13165 filed Dec. 22, 2005, the contents of all of which are incorporated herein by reference in their entirety.

The present invention relates to a device for determining the permeation properties of a hollow body made of a material that is permeable to at least one gaseous element.

The invention especially applies to the field of packaging, such as plastic containers, intended to contain a liquid food product, optionally under pressure.

By way of example, the plastic container is a polypropylene or PET (polyethylene terephthalate or polyethylene glycol terephthalate) bottle.

The term “permeation” is understood here to mean any physical and/or chemical phenomenon resulting in the passage of a gas through the object studied.

The term “permeation” is especially understood here to mean the leakage of a gaseous element through microcracks in the wall of the object studied, or else the diffusion of the gaseous element through the wall of the object studied.

In the tester devices known from the prior art, that are used to test substantially flat objects, a carrier gas, for example nitrogen, is circulated in a first chamber and a tester gas, for example oxygen, is circulated in a second chamber, the first and second chambers being separated by the wall of the object to be studied.

The stream from the chamber fed with carrier gas is sent to a chemical analysis apparatus, known per se, suitable for detecting the presence, or even measuring the amount of tester gas present in this stream.

This chemical analysis apparatus is, for example, a mass spectrometer.

When it is desired to study the permeation properties of a hollow body, such as a three-dimensional packaging made of a flexible material, in its geometry for subsequent use, it is known to place this hollow body in a tester gas atmosphere, and to circulate a carrier gas stream inside the hollow body, the stream that exits being conveyed to a detection and measurement apparatus. Reference may be made, for example, to documents U.S. Pat. No. 6,857,307 or US 2004/0040372.

It is of course impossible to place the hollow body under vacuum without irreversibly deforming it. Thus, in order to desorb the gaseous molecules present in the plastic of the hollow body, it is standard practise to circulate the carrier gas for several days in order to reach a steady state in which the permeation measurements may be carried out.

The time necessary to obtain this steady state is even longer when the wall thickness and/or internal volume of the hollow body is great.

In order to reduce this time for establishing a steady state, it has been proposed to reduce the pressure uniformly on either side of the wall of the hollow body.

The Applicant has observed that significant measurement errors may be linked to an artifact originating from a loss of sealing between the internal volume of the hollow body and the volume surrounding the hollow body.

The Applicant has observed, in particular, that when the hollow body to be studied has an opening especially such as a neck, which is the case, for example, for bottles, the conventional devices do not make it possible to guarantee a satisfactory sealing at the bottle neck.

The Applicant has set out to overcome these problems.

For this purpose, the invention relates, according to a first aspect, to a device for measuring the permeation of a hollow body provided with an opening such as, in particular, a neck, this device comprising a chamber in which the hollow body is placed on a support; this hollow body, when placed on its support delimiting with the chamber an inner space and an outer space, the device being provided with sealing means between the inner space and the outer space, the sealing means comprising three seals, namely a first seal, a second seal known as an intermediate seal, and a third seal, these three seals being housed in grooves of a body of the support, these seals jutting out relative to the side edge of the body of the support and being able and configured to bear against the inner face of the opening of the hollow body; the body of the support, the opening of the hollow body and the seals thus delimiting two spaces positioned between the inner space and the outer space, a first space being bordered by a first seal and an intermediate seal, the second space being delimited by the intermediate seal and a third seal.

The device has, according to several embodiments, the following, where appropriate combined, characters:

- the device comprises means that make it possible to maintain a given fluid pressure in the second space, said means advantageously comprising a duct inside the body of the support and connected to a source of compressed gas;
- the device comprises means that make it possible to detect a gas leak in the first space, a leak originating either from the second space, or from the chamber in which the hollow body is placed. One way that can be envisioned for controlling this leak may be to detect a pressure variation in said space, said means then advantageously comprising a duct inside the body of the support and that connects a pressure sensor to the first space; another way may be to detect a change in the composition or concentration of the gas contained in said space, said means then advantageously comprising a duct inside the body of the support and that connects a suitable detector such as a spectrometer to the first space;
- the body of the support is substantially cylindrical and three tiered annular grooves that house the seals are arranged at the periphery of the body of the support;
- the three seals are substantially identical and equidistant;
- the body of the support juts out from a base, this base being placed on a pedestal, a seal being placed between the base and the pedestal, two half shells covering the base and forming a support stand for a bell jar that delimits the chamber, the body of the support passing through a cutout in the half shells; and
- when the hollow body is in place, the pressure in the first space is substantially equal to atmospheric pressure, and the pressure in the second space is greater than the pressure in the inner space.

Other subjects and advantages of the invention will appear during the following description of one currently preferred embodiment, a description which will be made with reference to the appended drawings, in which.

Figure 1:
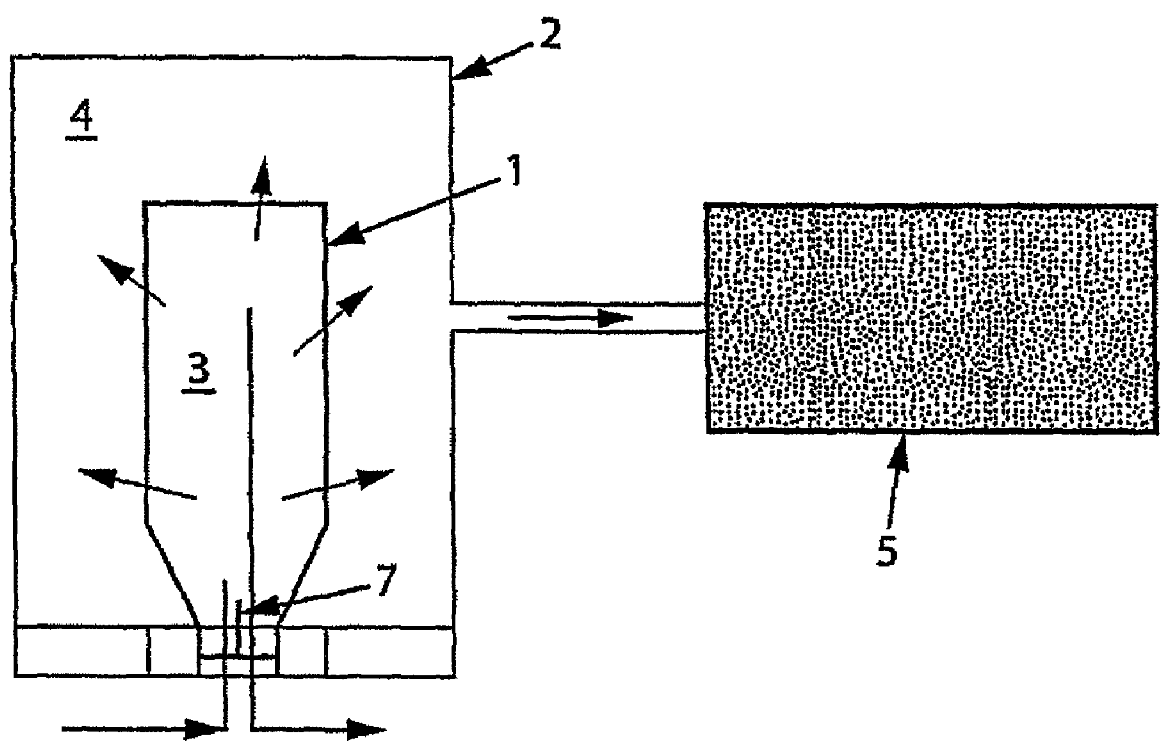
FIG. 1 is a schematic diagram of a measurement installation in which the invention may be carried out.

Reference will be made to FIG. 1.

Represented in this FIG. 1 is a hollow body 1 placed in a chamber 2. This hollow body 1 thus delimits an inner space 3 and an outer space 4 which are separated from one another. More specifically, the inner space 3 is formed by the inside of the hollow body 1 and the outer space 4 is that which surrounds the hollow body 1 in the chamber 2. A support 7, which will be explained in detail later on, holds the hollow body 1 and isolates it from the outside. A tester gas, such as for example helium, is introduced into the inner space 3. The pressure in the inner space 3 is, for example, around 1 bar.

The outer space 4 is connected to a detection and measurement apparatus, such as a mass spectrometer 5.

The outer space 4 is placed under vacuum relative to the inner space 3 so that, when the hollow body 1 to be tested is permeable, a migration of the gas that it contains is promoted in the direction of the outer space 4, which causes a change in the composition of the tester gas that can be detected by the mass spectrometer 5.

Figure 2:
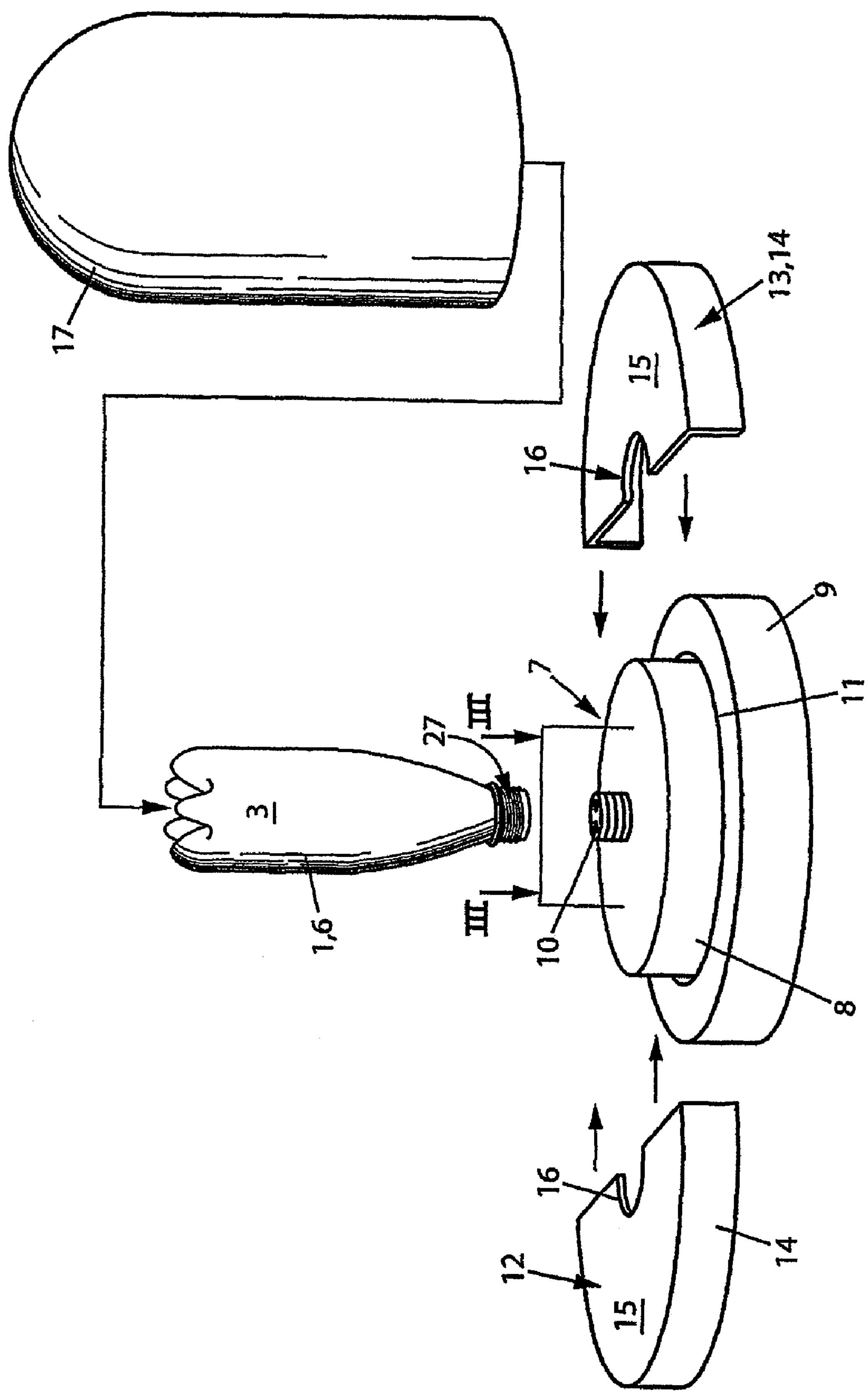
FIG. 2 is a perspective view of an implementation mode of the invention.
Figure 3:
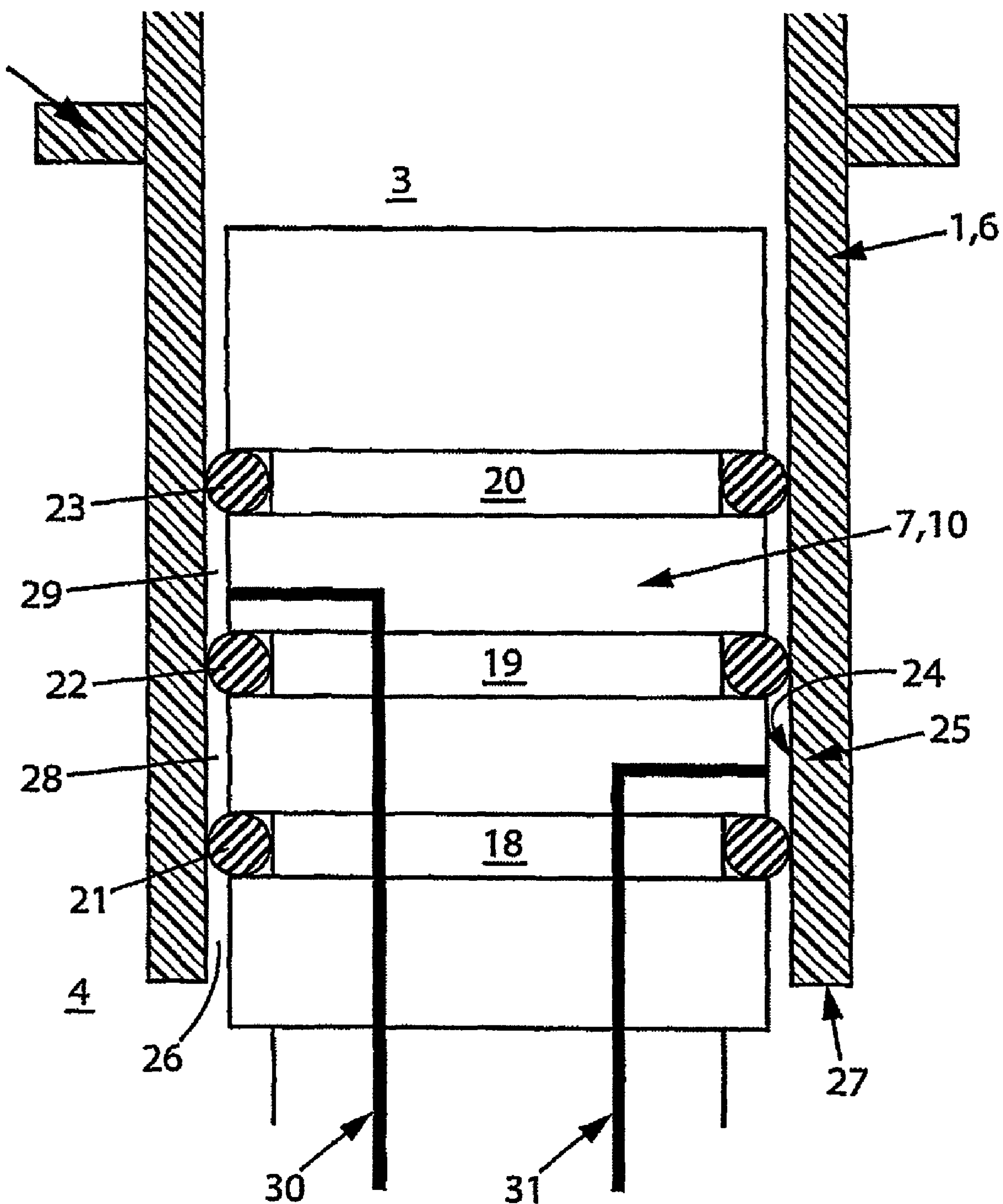
FIG. 3 is a longitudinal cross-sectional view along the plane III-III from FIG. 2.

Reference will now be made to FIG. 2.

A hollow body 1 such as a bottle 6 is intended to be placed, neck down, onto a support 7. This support 7 comprises a base 8, a pedestal 9 and a support body 10 that juts out to receive the hollow body 1.

The base 8 is disk-shaped and rests on the pedestal 9. An O-ring 11 is placed on the lower part of the base 8. A cowling, formed from two half shells 12, 13 covers the base 8. For this purpose, each half shell comprises a skirt 14 and an upper part 15 transverse to the skirt 14. Each half shell is also equipped with a cutout 16 through which the support projection 10 passes.

The outer space 4 is delimited by a bell jar 17 which rests on the cowling formed by the two half shells 12, 13.

The means that make it possible to maintain a satisfactory seal between the inner space 3 and the outer space 4 will now be described.

The body 10 of the support 7 is of cylindrical shape and is equipped with three tiered outer annular grooves 18, 19, 20.

Each of these three grooves 18, 19, 20 houses a seal 21, 22, 23. The seals bear against the inner face 24 of the neck 25 of the hollow body 1, the neck being constituted here by the throat of the bottle 6, when this bottle 6 is forced over the body 10 of the support 7. This is because the seals 21, 22, 23 jut out beyond the side edge of the body 10 of the support 7.

In one implementation, as represented, the seals 21, 22, 23 are substantially identical.

Underneath the first lower seal 21, in the space 26 next to the lip 27, the pressure of the outer space 4 prevails.

Between the first lower seal 21 and the second intermediate seal 22 an annular space 28 is delimited in which atmospheric pressure prevails, which is none other than ambient pressure when the neck 25 is forced over the body 10 that juts out from the support 7.

Between the second intermediate seal 22 and the third upper seal 23 an annular space 29 is delimited in which a controlled pressure prevails. Advantageously, this controlled pressure is greater than the pressure in the inner space 3 (above the third seal 23).

For this purpose, a first duct 30 keeps a gas, for example air, under pressure in the space 29, this duct 30 comprising a lower axial part inside the body 10 and an upper radial part that emerges between the second seal 22 and the third seal 23.

Advantageously, a second duct 31 connects the annular space 28, in which a pressure equal to atmospheric pressure prevails, to a leakage sensor such as a pressure sensor (not represented). This duct 31 comprises a lower axial part inside the body 10 of the support 7 and an upper radial part that emerges between the first joint 21 and the second joint 22. The pressure sensor makes it possible to detect a loss of sealing between the first and the second seal and also a loss of sealing between the second and the third seal, and consequently between the inner space 3 and the outer space 4. Instead of the pressure sensor, a gas composition or concentration detector, such as a spectrometer, could be used in order to detect a change in the composition, symptomatic of a modification of the nature of the gas in the space 28, linked to a leak, especially between the inner space 3 and the outer space 4.

It is understood that the terms "first", "second", "third", "lower", "intermediate" and "upper" are not limiting.

These terms are used in order to facilitate the reading of this description for the seals 21, 22, 23 with reference to the positioning of the neck 25 with its opening pointing downward, the body 10 of the support that juts out being oriented toward the top of the device.

This orientation corresponds to that which is conventional in commercial devices, which in fact facilitates the positioning and holding of the bell jar 17.

The invention claimed is:

1. A device for measuring the permeation of a hollow body provided with an opening, the device comprising a chamber in which the hollow body is placed on a support; the hollow body, when placed on said support delimiting with said chamber an inner space and an outer space, the device being provided with sealing means between said inner space and outer space, wherein said sealing means comprise three seals, which are respectively a first seal, a second or intermediate seal, and a third seal, said three seals being housed in grooves of a body of said support, said seals jutting out relative to a side edge of said body of said support and being arranged to bear against an inner face of the opening of the hollow body; said body of said support, the opening of the hollow body and said seals thus delimiting two spaces positioned between said inner space and said outer space, and one of which is a first space, which is bordered by said first seal and said intermediate seal, and the other of which is a second space which is delimited by said intermediate seal and said third seal.

2. The device for measuring the permeation of a hollow body as claimed in claim 1, further comprising pressure means that make it possible to maintain a given fluid pressure in said second space.

3. The device for measuring the permeation of a hollow body as claimed in claim 2, wherein said pressure means comprise a first duct inside said body of said support and connected to a source of compressed gas.

4. The device for measuring the permeation of a hollow body as claimed in claim 1, further comprising detecting means that make it possible to detect a gas leak in said first space.

5. The device for measuring the permeation of a hollow body as claimed in claim 4, wherein said detecting means comprises a second duct inside said body of said support and a pressure sensor connected via said second duct to said first space.

6. The device for measuring the permeation of a hollow body as claimed in claim 4, wherein said detecting means comprises a second duct inside said body of said support and a gas composition or concentration sensor connected via said second duct to said first space.

7. The device for measuring the permeation of a hollow body as claimed in claim 1, wherein said body of said support is substantially cylindrical and three tiered annular grooves that respectively house said three seals are arranged at the periphery of said body.

8. The device for measuring the permeation of a hollow body as claimed in claim 7, wherein said three seals are substantially identical and equidistant to each other.

9. The device for measuring the permeation of a hollow body as claimed in claim 1, wherein said body of said support juts out from a base, which is placed on a pedestal, a seal being placed between said base and said pedestal, two half shells covering said base and forming a support stand for a bell jar that delimits said chamber, said body of said support passing through a cutout in said half shells.

10. The device for measuring the permeation of a hollow body as presented in claim 1, wherein the pressure in said first space is substantially equal to atmospheric pressure, and the pressure in said second space is greater than that in said inner space.

* * * * *